(12) United States Patent
Kim et al.

(10) Patent No.: US 6,706,849 B2
(45) Date of Patent: Mar. 16, 2004

(54) GLYCIDYL DI-NITROPROPYL CARBONATE AND POLY (GLYCIDYL DI-NITROPROPYL CARBONATE)

(75) Inventors: Jin Seuk Kim, Daejeon (KR); Jin Rai Cho, Daejeon (KR); Keun Deuk Lee, Daejeon (KR); Bang Sam Park, Daejeon (KR)

(73) Assignee: Agency for Defense Development, Daejeon (KR)

( * ) Notice: Subject to any disclaimer, the term of this patent is extended or adjusted under 35 U.S.C. 154(b) by 0 days.

(21) Appl. No.: 10/340,504

(22) Filed: Jan. 10, 2003

(65) Prior Publication Data

US 2003/0225245 A1 Dec. 4, 2003

(30) Foreign Application Priority Data

May 8, 2002 (KR) ........................................ 2002-25361

(51) Int. Cl.⁷ ............................................... C08G 64/00
(52) U.S. Cl. ........................ 528/196; 149/19.1; 528/198
(58) Field of Search .......................... 149/19.1; 528/196, 528/198

(56) References Cited

U.S. PATENT DOCUMENTS 4,139,403 A * 2/1979 Baum et al. .................. 149/88

* cited by examiner

*Primary Examiner*—Terressa Boykin
(74) *Attorney, Agent, or Firm*—Scully, Scott & Murphy & Presser

(57) ABSTRACT

Disclosed are glycidyl di-nitropropyl carbonate and poly (glycidyl di-nitropropyl carbonate) which is prepolymer used as an energetic binder for an insensitive and high performance explosive. The present invention introduces the nitro group instead of the nitrate group, thereby enabling to provide the prepolymer having the high thermal stability (thermal decomposition initiating temperature of at least 200° C. or higher) more excellent than that of the conventional energy binder.

2 Claims, No Drawings

GLYCIDYL DI-NITROPROPYL CARBONATE AND POLY (GLYCIDYL DI-NITROPROPYL CARBONATE)

BACKGROUND OF THE INVENTION

1. Field of the Invention

The present invention relates to glycidyl di-nitropropyl carbonate and poly(glycidyl di-nitropropyl carbonate), and more particularly, to poly(glycidyl di-nitropropyl carbonate) which is prepolymer used as an energetic binder for an insensitive and high performance explosive.

2. Background of the Related Art

There is a prepolymer of hydroxyl-terminated polybutadiene(HTPB) used widely as a binder of a plastic-bonded explosive(PBX) according to a related art. The binder is included in about 15% of PBX so as to improve a mechanical property. Yet, the binder is an inert material, thereby reducing energy of PBX. Hence, many efforts are made to develop an energetic binder for increasing the energy of PBX. As a result of such efforts, various energetic binders have been developed such as {poly(glycidyl nitrate)}(PGN), {poly(3-nitratomethyl-3-methyloxetane)}(PNMMO), and the like. However, they show poor thermal stability since the thermal decomposition initiating temperature by each prepolymer containing a nitrate group(—$ONO_2$) as an energy group appears at about 180° C.

Therefore, the inventors of the present invention has made many efforts to improve the thermal stability of the energetic binder in a manner that a nitro group(—$NO_2$) is introduced instead of the nitrate group as well as hydrogen is removed so as not to resolve the nitro group by considering the fact that the hydrogen adjacent to the nitrate group accelerates the chain scission reaction of polyurethane elastomers in PGN.

SUMMARY OF THE INVENTION

Accordingly, the present invention is directed to glycidyl di-nitropropyl carbonate and poly(glycidyl di-nitropropyl carbonate) that substantially obviate one or more problems due to limitations and disadvantages of the related art.

An object of the present invention is to provide glycidyl di-nitropropyl carbonate used as a monomer of an energy binder and poly(glycidyl di-nitropropyl carbonate) used as a prepolymer by introducing a nitro group and removing hydrogen accelerating a resolution reaction.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof.

To achieve these objects and other advantages and in accordance with the purpose of the invention, as embodied and broadly described herein, glycidyl di-nitropropyl carbonate according to the present invention is represented by the following chemical formula 1:

[Chemical Formula 1]

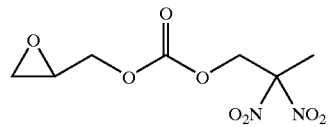

(I)

In another aspect of the present invention, poly(glycidyl di-nitropropyl carbonate) is represented by the following chemical formula 2:

[Chemical Formula 2]

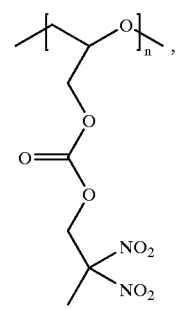

(II)

wherein a molecular weight is 2,000–3,500.

It is to be understood that both the foregoing general description and the following detailed description of the present invention are exemplary and explanatory and are intended to provide further explanation of the invention as claimed.

DETAILED DESCRIPTION OF THE INVENTION

Reference will now be made in detail to the preferred embodiments of the present invention.

The present invention relates to glycidyl di-nitropropyl carbonate represented by the following chemical formula 1 and poly(glycidyl di-nitropropyl carbonate) represented by the following chemical formula 2. In this case, poly(glycidyl di-nitropropyl carbonate) has a molecular weight of 2,000–3,500.

[Chemical Formula 1]

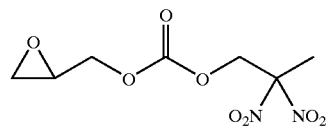

(I)

[Chemical Formula 2]

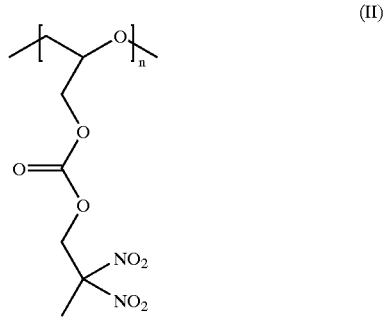

A compound (I) according to the chemical formula 1 and another compound (II) according to the chemical formula 2 as new substances according to the present invention can be prepared by the following method.

First of all, 2,2-dinitropropanol is dissolved in methylene chloride of an anhydrous solvent so as to be mixed well. And, pyridine is added thereto. In this case, any kind of the anhydrous solvent can be used. Yet, methylene chloride having a low boiling point is preferable to separate the solvent from polymer of high viscosity after polymerization. Allyl chlorofomate dissolved in methylene chloride is added to the mixture for two hours by controlling its injection speed under the condition that 0° C.–30° C. is maintained, whereby 2,2-dinitropropanol and allylchlorofomate react to each other with the existence of pyridine. Thereafter, additional reaction is carried out thereon for three hours at room temperature. After the reaction, methylene chloride and distilled water are added thereto so as to extract methylene chloride. The extract is washed several times through an HCl solution, a NaOH solution, and a NaCl saturated solution. The washed extract is dehydrated by magnesium sulfate. This solution is filtered, the solvent is removed therefrom, and then volatile materials are completely removed by decompression. Thus, allyl dinitropropyl carbonate is attained.

The attained allyl dinitropropyl carbonate is dissolved in methanol, hydroperoxide is added thereto, and then NaOH is put into by maintaining a reaction temperature of 15° C.–20° C. In this case, it is difficult to control the reaction if the temperature exceeds 30° C. After all the injections have been made, the reaction is carried out while the reaction temperature is maintained at the temperature of 20° C.–25° C. After the end of the reaction, water is added thereto so as to carry out extraction several times using methylene chloride. This solution is washed by a NaCl saturated solution, and then dehydrated with anhydrous magnesium sulfate. This solution is filtered, the solvent is removed therefrom, and then volatile materials are completely removed by decompression. Thus, the target compound (I) of the chemical formula according to the present invention is attained.

The above-attained compound (I) dissolved in methylene chloride is added for about three hours to the solution from which ether is completely removed by carrying out decompression on boron trifluoride etherate into which 1,4-butanediol is put. After polymerization, a washing process is carried out thereon by adding water and methylene chloride thereto, this solution is washed again by a NaCl saturated solution, and dehydration is carried out thereon with anhydrous magnesium sulfate. Ethanol is added to this polymer, and agitation is carried out thereon so as to wash out organic materials failing to react, volatile materials are completely removed by decompression. Thus, the target compound (II) of the chemical formula 2 according to the present invention is attained.

Such a preparation method is represented by the following chemical equation 1.

[Chemical Equation 1]

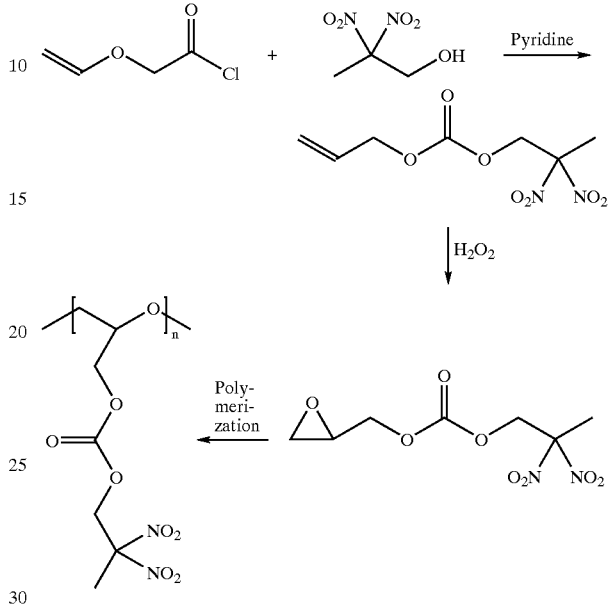

Embodiments according to the present invention are explained in detail as follows. The forgoing embodiments are merely exemplary and are not to be construed as limiting the present invention.

[Embodiments]

First Embodiment: Synthesis of Allyl Dinitropropyl Carbonate

First of all, 123.5 g (0.823 mole) of 2,2-dinitropropan-1-ol(DNP-OH) is dissolved in 412 g of methylene chloride so as to be mingled with each other well at 0° C., and then 69 g of pyridine is added thereto for about 10 minutes. And, 104 g of allyl chlorofomate is dissolved in 104 g of methylene chloride so as to be added to the mixture for two hours. In this case, the injection rate is controlled to maintain a temperature of the reaction solution at 5° C.–10° C. After the injection, additional reaction is carried out thereon for three hours at the room temperature so as to complete the reaction. After completion of the reaction, 200 ml of methylene chloride is added thereto, 600 ml of distilled water is put into the solution, and then extraction is carried out thereon with methylene chloride. The extract is washed twice by 500 ml of a 5% HCl solution, four timed by 500 ml of a NaOH solution, and twice by 500 ml of a NaCl saturated solution. The extract is then dehydrated by magnesium sulfate. This solution is filtered, the solvent is removed therefrom, and then volatile materials are completely removed by decompression at 10 mmHg/60° C. for five hours.

As a result, 182.8 g of allyl 2,2-dinitropropyl carbonate is attained with 97% yield.

$^1$H-NMR(CDCL$_3$): 2.19(CH$_3$, singlet), 4.62(CH$_2$, doublet), 4.93(CH$_2$, singlet), 5.3(CH$_2$, multiplet), 5.85(CH, multiplet)

Second Embodiment: Synthesis of Glycidyl Dinitropropyl Carbonate

First of all, 23.5 g (0.1 mol) of allyl dinitropropyl carbonate is dissolved in 100 ml of methanol, 27 ml (0.11 mol)

of 35% $H_2O_2$ is added thereto, and a temperature of a reaction solution is set up as 15° C. 9.1 ml (55 mmol) of 6N NaOH is added to this reaction solution by controlling an injection rate just to maintain the temperature of the reaction solution at 15° C.–20° C. The reaction is carried out for three hours by maintaining the temperature of the reaction solution at 20° C.–25° C. after the end of the injection, whereby the reaction is completed. After the completion of the reaction, 100 ml of water is added thereto, and then extraction is carried out three times with 100 ml of methylene chloride. This solution is washed twice by 100 ml of a NaCl saturated solution, and then dehydrated with anhydrous magnesium sulfate. This solution is filtered, the solvent is removed therefrom, and then volatile materials are completely removed by decompression at 10 mmHg/60° C. for five hours.

As a result, 18.4 g of glycidyl dinitropropyl carbonate is attained with 75% yield.

$^1$H-NMR(CDCL$_3$): 2.19(CH$_3$, singlet),; 2.84, 2.89(CH$_2$, triplet), 3.21(CH, multiplet), 4.0, 4.4(CH$_2$, quartet), 4.94 (CH$_2$, singlet)

Third Embodiment: Synthesis of Poly(glycidyl Dinitropropyl Carbonate)

First of all, 0.18 g (2 mmol) of 1,4-butanediol is put into 0.28 g (2 mmol) of boron trifluoride etherate(BF$_3$.OEt$_2$), decompression is carried out thereon just to remove ether completely, and then 12 g of methylene chloride is added thereto. And, 12 g (50 mmol) of glycidyl dinitropropyl carbonate synthesized by the second embodiment of the present invention are dissolved in methylene chloride so as to be added to the above solution for about three hours. After the polymerization, 50 ml of water and 30 ml of methylene chloride are added thereto so as to wash the solution. This solution is washed twice by 50 ml of a NaCl saturated solution, and then dehydrated with anhydrous magnesium sulfate. This polymer into which 20 ml of ethanol is put is agitated just to wash out organic substances failing to react, and then decompression is carried out thereon at 1 mmHg/ 80° C. for five hours so as to remove volatile materials completely.

A polymerization rate of the produced polymer is about 91%, and prepolymer having 2,200 of mean value molecular weight, dispersity of 1.32, 1.98 of functionality, (–)21° C. of glass transition temperature, and 210° C. of thermal decomposition initiating temperature.

The energy binder according to the related art uses a nitrate group as an energy group, thereby showing low thermal stability (thermal decomposition initiating temperature of about 180° C.). Yet, the present invention introduces the nitro group instead of the nitrate group, thereby enabling to provide the prepolymer having the thermal stability (thermal decomposition initiating temperature of at least 200° C. or higher) more excellent than that of the conventional energy binder. Moreover, the present invention uses the inexpensive initiating and intermediate materials as well as provides a high yield of the product, thereby being economical.

The forgoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A glycidyl di-nitropropyl carbonate represented by the following chemical formula 1:

[Chemical Formula 1]

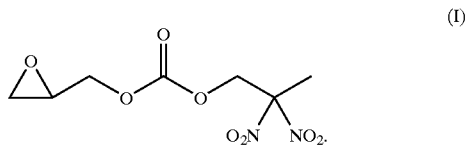

(I)

2. A poly(glycidyl di-nitropropyl carbonate) represented by the following chemical formula 2:

[Chemical Formula 2]

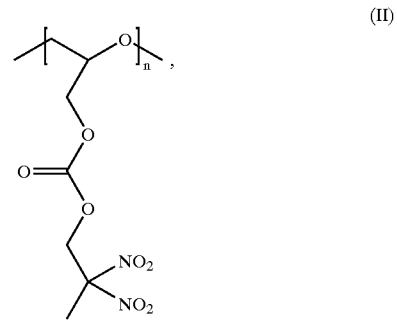

(II)

wherein a molecular weight is 2,000–3,500.

* * * * *